US009655836B2

(12) United States Patent
Streuli

(10) Patent No.: US 9,655,836 B2
(45) Date of Patent: May 23, 2017

(54) SPRAYABLE COMPOSITION COMPRISING HIGH MOLECULAR WEIGHT CHARGED POLYMER

(75) Inventor: David C. Streuli, Wayne, NJ (US)

(73) Assignee: ISP INVESTMENTS LLC, Wilmington, DE (US)

(*) Notice: Subject to any disclaimer, the term of this patent is extended or adjusted under 35 U.S.C. 154(b) by 381 days.

(21) Appl. No.: 13/639,369

(22) PCT Filed: Apr. 4, 2011

(86) PCT No.: PCT/US2011/031088
§ 371 (c)(1),
(2), (4) Date: Dec. 4, 2012

(87) PCT Pub. No.: WO2011/126978
PCT Pub. Date: Oct. 13, 2011

(65) Prior Publication Data
US 2013/0129657 A1 May 23, 2013

Related U.S. Application Data

(60) Provisional application No. 61/321,746, filed on Apr. 7, 2010.

(51) Int. Cl.
*A61K 8/81* (2006.01)
*A61K 8/04* (2006.01)
(Continued)

(52) U.S. Cl.
CPC ............ *A61K 8/8182* (2013.01); *A61K 8/046* (2013.01); *A61K 8/8147* (2013.01);
(Continued)

(58) Field of Classification Search
None
See application file for complete search history.

(56) References Cited

U.S. PATENT DOCUMENTS

2009/0098079 A1* 4/2009 Schiemann ............ A61K 8/046
424/70.11
2010/0068156 A1* 3/2010 Kim ...................... A61K 8/8111
424/45

FOREIGN PATENT DOCUMENTS

DE WO 2009059815 A2 * 5/2009 ........... A61K 8/8117

OTHER PUBLICATIONS

English translation for WO 2009/059815 A2, Scheffler et al., May 14, 2009.*

(Continued)

*Primary Examiner* — Carlos Azpuru
*Assistant Examiner* — Casey Hagopian
(74) *Attorney, Agent, or Firm* — William J. Davis

(57) ABSTRACT

Disclosed herein are sprayable compositions comprising: a complex of (A) at least one charged (or pseudo-charged) polymer having a molecular weight of about 125,000 amu or more; and (B) a least one oppositely charged, rheology modifying, crosslinked polymer having at least one carboxylic functional group. The composition may provide a spray with a median particle size of less than about 175 μm. Also disclosed are methods for preparing the compositions as well as creating the spray. The invention enables the spray of the high molecular weight charged (or pseudo-charged) polymer in any number of uses including personal care and performance chemicals application.

9 Claims, 6

(51) Int. Cl.
    *A61Q 5/00*    (2006.01)
    *A61Q 5/06*    (2006.01)
(52) U.S. Cl.
    CPC .......... *A61K 8/8152* (2013.01); *A61K 8/8164* (2013.01); *A61Q 5/06* (2013.01); *A61K 2800/5424* (2013.01); *A61K 2800/5426* (2013.01); *A61K 2800/594* (2013.01)

(56) References Cited

OTHER PUBLICATIONS

PCT, International Search Report, International Application No. PCT/US2011/031088 (mailed May 25, 2011; published Oct. 13, 2011).

* cited by examiner

SPRAYABLE COMPOSITION COMPRISING HIGH MOLECULAR WEIGHT CHARGED POLYMER

FIELD

The invention relates to sprayable compositions of high molecular weight charged polymer, and methods for preparing and actuating the sprayable compositions.

BACKGROUND

Hair spray is a styling and beautifying aid used by 65% of women over the age of thirteen. Around 70% of these women use hair spray daily. Consumers require hair sprays to perform in holding their hairstyle and also to contribute to beautifying the appearance of their hair. People who perm and color their hair are also concerned that the hair spray will not dull the color of their hair or weigh down their curls. Further, these hairspray compositions must meet a number of functional requirements. These include good holding ability and curl retention without giving a harsh, brittle feeling to the hair. Even under humid conditions there must be good hold and curl retention. Additionally, the compositions must include the properties of low stickiness and a lack of powdering or flaking. Most of these hair spray compositions contain homo or copolymers as the active ingredients in addition to a carrier. The homopolymers and non-homopolymers are prepared from variety of monomers for example, vinyls, acrylics, acrylamides, unsaturated mono/di carboxylic acids and/or acid anhydrides. Depending upon selection of monomers, the resulting polymers can be anionic, cationic, pseudo-anionic, pseudo-cationic, and amphoteric in nature.

Many people desire a high level of style retention, or hold, from a hair spray composition. In typical hair sprays, performance attributes and product aesthetics are often answered by large molecules with high molecular weight charged polymers or resins having molecular weight of about 125,000 atomic mass units (amu) or more. The attributes of these large molecules can easily be achieved by easily incorporating them into various products and applications wherein the actuation is not required or involved for example gels, creams and mousses etc.

Unfortunately, the delivery of such high molecular weight polymers or resins, such as those having a weight average molecular weight of greater than about 125,000 amu in aerosol and pump spray formulations has been difficult even under pressure to deliver a uniform spray. In fact, they tend to have spray patterns characterized by wet drippy centers or to have spray characterized by streaming rather than a fine misting of hair spray particles. The difficulties in spraying high molecular weight polymers includes practical concerns, including clogging, poor product aesthetics, for example foam quality, cushion/feel, distribution etc. and poor performance attributes such as thermal protection, durability, conditioning, water resistivity etc. Further, most of the hair sprays have been usually formed with high percentage of monohydric alcohol solvents, such as lower alcohols and low amounts of water that results in formulation having poor quality of sprayability. Further, consumers are also conscious of environmental issues and expect their products to comply with regulations without sacrificing performance.

U.S. patent application 2007/0141013 discloses ampholytic copolymers which contain a molar excess of anionogenic and/or anionic groups, polyelectrolyte complexes which contain such an ampholytic copolymer, cosmetic and pharmaceutical compositions which contain at least one such copolymer or polyelectrolyte complex and the use of these copolymers and polyelectrolyte complexes are described.

U.S. patent application 2006/0183822 discloses an ampholytic copolymer, polyelectrolyte complexes which comprise such an ampholytic copolymer, and cosmetic or pharmaceutical compositions which comprise at least one ampholytic copolymer or one polyelectrolyte complex.

U.S. patent application 2001/0022967 discloses a hair styling composition comprising: (a) less than about 1.5% active of one or more holding polymers, (b) one or more saccharides, having monomeric units greater than two, and (c) a carrier.

U.S. patent application 2003/0008855 discloses anti-dandruff hair styling composition containing at least one active ingredient for the treatment of dandruff and/or seborrheic dermatitis; at least one thickening agent; and at least one a hair styling resin. In a preferred embodiment, the hair styling composition is in the form of a gel that suspends the active ingredient. The publication also provides a method of treating hair or scalp using the described composition.

U.S. patent application 2006/0134049 on hair styling composition that relates to compositions and methods for treating and modifying hair. More particularly, the application is directed to styling and conditioning compositions for modifying and fixing hair comprising one or more rheology modifiers and one or more hair styling resins and a method of using the compositions to modify, condition and fix hair.

U.S. patent application 2006/0251603 by ISP Investments Inc on mending hair damage with polyelectrolyte complexes teaches about complexed form of anionic and cationic polymers that are used to mend damaged hair fibers, especially damage exhibited by split ends. An improved test method designed for the assessment of the degree of split end repair is described which consists of tagging hair fibers and observing the repair process by stereomicroscopy.

In view of forgoing facts, there remains a desire to develop a homogenously sprayable composition comprising high molecular weight charged polymers, particularly, hair care composition comprising effective use levels of high molecular weight polymers or resins having minimum amount of alcoholic component. Also it is desired to have a sprayable hair care composition capable of imparting enhanced product aesthetics and performance attributes for the users.

SUMMARY

In one aspect the invention provides sprayable compositions comprising one or more charged polymers having a molecular weight of about 125,000 amu or more. The sprayability is enabled through the complexation of the high molecular weight charged polymer(s) with one or more oppositely charged, rheology modifying, crosslinked polymers. The sprayable compositions find application in numerous arts, including personal care and performance chemicals applications. Preferred, but non-limiting, personal care compositions are hair sprays.

In a second aspect the invention discloses methods for producing a uniform, sprayable complex comprising a high molecular weight polymer having a molecular weight of about 125,000 amu or more and an oppositely charged, rheology modifying, crosslinked polymer.

In yet another aspect the invention also provides a spray of the abovementioned sprayable complex.

Another aspect of the invention is provided for enhancing the on-hair performance of hair spray compositions by using the taught compositions and methods.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein.

DETAILED DESCRIPTION

Figure 1:
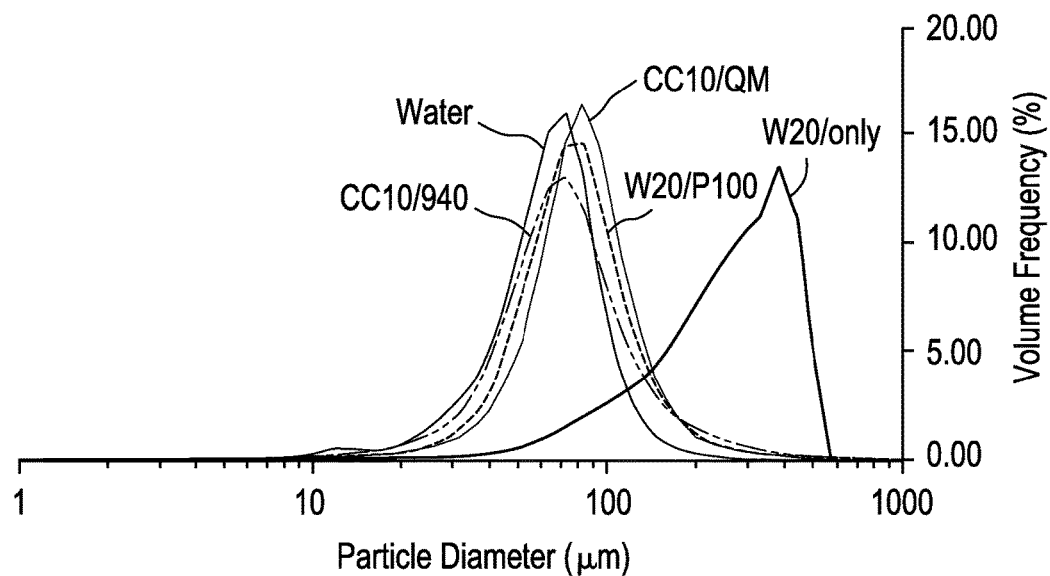
FIG. 1 is a graphical illustration of particle size distribution of compositions of Example 2.

While this specification concludes with claims particularly pointing out and distinctly claiming that, which is regarded as the invention it is anticipated that the invention can be more readily understood through reading the following detailed description of the invention and study of the included examples.

When introducing elements of the present invention or the preferred embodiments(s) thereof, the articles "a", "an", "the" and "said" are intended to mean that there are one or more of the elements. The terms "comprises", "comprising", "including", "includes", "has" and "having" or any other variations thereof are intended to be inclusive and mean that there may be additional elements other than the listed elements.

The term "about" refers to a difference of 10% from the value specified. Numerical ranges as used herein are meant to include every number and subset of numbers enclosed within that range, whether particularly disclosed or not. All percentages, parts, proportions and ratios as used herein, are by weight of the total composition, unless otherwise specified.

The term "atomize" or "spray" refers to the release of the product in the form of dissipated particles and wherein the dissipated particles can have different shapes, consistencies, and sizes. The properties of the dissipated particles can include fine aerosol atomized spray to liquid drops, snow-like drops, solid spray flakes, and sprays foam.

The term "effective amount" or "effective use level" of high molecular weight charged polymer refers to sufficient amount of high molecular weight charged polymer employed to provide desired performance attributes and product aesthetics. Examples of useful properties include, but are not limited to, thermal protection, durability conditioning, water resistivity, quality, cushion feel, distribution etc. and wherein the high molecular weight polymer is adequately actuated.

The term "halogen" refers to chloro, bromo, iodo and fluoro, and is preferably bromo or chloro.

The term "monomer" refers to the repeat units that comprise a polymer. A monomer is a compound that chemically bonds to other molecules, including other monomers, to form a polymer.

The term "polymer" refers to both linear and branched polymers derived from one or more monomer units, which may or may not be crosslinked, or grafted. Non-limiting examples of polymers include copolymers, terpolymers, tetramers, and the like, wherein the polymer is random, block, or alternating polymer.

The term "homopolymer" refers to a molecule that comprises one type of monomer, and includes such polymers wherein a small amount of polymerization solvent may be covalently bonded into the polymer.

The term "non-homopolymer" refers to a polymer that comprises more than one type of monomer, and includes such polymers wherein a small amount of polymerization solvent may be covalently bonded into the polymer. The non-homopolymer is copolymers, terpolymers, tetramers, and the like.

The term "cationic polymers" refers to polymers displaying at least one primary amine, secondary amine or tertiary amine or quaternary ammonium group in their principal chain or branched chain or in the substituted form. Generally, these cationic polymers employed in the compositions of the present invention have a molecular weight of at least about 125,000 amu or MOM.

The term "complex" refers to a complex formed upon the reaction or interaction of a high molecular weight charged polymer with a rheology modifying agent. "Complex" as used herein refers to the substance resulting from the reaction of selected ingredients regardless of the specific mechanism involved to result in the complex.

As used herein, the term "hydroalcoholic" refers to solvents based on $C_1$ to $C_4$ lower alcohols mixed with water. In accordance with certain aspects, the proportion of lower alcohol and water may be 10:90 to 90:10. Examples of specific lower alcohols include but are not limited to ethanol, 2-propanol, and n-propanol.

The expression "rheology modifying" as used herein with reference to a polymer deals with the property of the polymer to change the rheological properties of a given composition. The rheological properties that may be changed include, but are not limited to, sprayability, solution viscosity, gelation, viscosity changes under shear stress, foam stabilization, gel pick-up in presence of said polymer.

"High molecular weight charged polymer" refers to a cationic or anionic polymer having a minimum molecular weight (weight average MW) of at least about 125,000 amu, more particularly at least about 250,000 amu, 500,000 amu, 750,000 amu, and in some cases at least 1,000,000 amu. Included in this definition are polymers having pseudo-cationic (e.g., non-quaternized amine, such as Styleze® CC-10 or Copolymer 937 sold by International Specialty Products) or pseudo-anionic character. The terms "pseudo-cationic polymers" and "pseudo-anionic polymers" refer to polymers that do not possesses an inherent positive or negative charge, but do possess behavior similar to charged polymers. The pseudo-charged behavior arises in these polymers due to electron donating or electron receiving atoms and/or groups within the polymer.

The upper limit of molecular weight of these polymers is limited by (i) solubility or dispersibility of the polymer in the selected solvent, and/or (ii) feasibility to form complexes with rheology-modifying crosslinked polymer. The high molecular weight charged polymer may be a solution polymer, latex polymer or gel polymer. The high molecular weight polymer may also be a structurally tailored homopolymer or non-homopolymer prepared by appropriate methods that are known in the art.

The patents and publications referred to herein are hereby incorporated by reference to the extent necessary to understand the present invention.

According to the present invention, sprayable compositions comprising high molecular weight anionic or cationic charged polymers and a processes for preparing the polymers are disclosed. The sprayability of a high molecular weight charged polymer may be achieved by means of a complex of (A) an effective amount of high molecular weight charged polymers having a molecular weight of at least about 125,000 amu or more; and (B) an oppositely charged rheology modifying crosslinked polymer containing at least one carboxylic functional group.

According to the present invention, sprayable hair care compositions of high molecular weight anionic or cationic charged polymers and a process for preparing the compositions are disclosed. The sprayability of a high molecular weight charged polymer in a hair care composition may be achieved by means of a complex of (A) an effective amount of high molecular weight charged polymers having a molecular weight of at least about 125,000 amu or more; and (B) an oppositely charged rheology modifying crosslinked polymer containing at least one carboxylic functional group.

In accordance with one embodiment of the present invention, the ratio or proportion of effective amount of high molecular weight charged polymers is from about 0.5% to about 5.0% (w/w), while the addition level of rheology modifying crosslinked polymer is from about 0.1% to 1.25% (w/w).

In accordance with some embodiments of the present invention, the ratio or proportion of effective amount of high MW charged polymers and rheology modifying crosslinked polymer may be about (0.1 to 1.0):(0.1 to 1.0).

The effective use levels of high molecular weight polymers suitable for producing the desired performance attributes and product aesthetics may be greater than or equal to about 1% (w/w) of the total sprayable composition and in some cases the use level of high molecular weight polymer may be about 1% to about 5% (w/w).

The high molecular weight charged polymers of the present invention may be selected from the group including, but not limited to, linear or branched anionic/cationic/pseudo-cationic homopolymer or copolymer or terpolymer and more particularly the rheology modifying polymer may be selected from the group including, but not limited to, crosslinked homopolymers or copolymers or terpolymers that belong to anionic or cationic or pseudo-cationic category.

In accordance with certain aspects, the sprayable composition disclosed herein includes a cationic/pseudo-cationic polymer obtained by polymerizing of one or more monomers selected from N-vinyl lactams, imidazoles, and α,β-ethylenically unsaturated monomers having at least one cationic group, quaternized amino alkyl acrylamides or their salts, and blends thereof.

In a particular embodiment, the homopolymer or non-homopolymer may be prepared by polymerizing a vinyl-substituted hetero-aromatic compound with a comononter and wherein the vinyl-substituted hetero-aromatic compound may be selected from N-vinyl lactams or N-vinyl imidazoles. The N-vinyl lactam derivatives may, for example, have one or more $C_1$-$C_6$ alkyl substituents, such as methyl, ethyl, n-propyl, isopropyl, n-butyl, sec-butyl, tert-butyl, etc. These include, for example, N-vinyl-2-pyrrolidone, N-vinyl-2-piperidone, N-vinyl-2-caprolactam, N-vinyl-5-methyl-2-pyrrolidone, N-vinyl-5-ethyl-2-pyrrolidone, N-vinyl-6-methyl-2-piperidone, N-vinyl-6-ethyl-2-piperidone, N-vinyl-7-methyl-2-caprolactam, N-vinyl-7-ethyl-2-caprolactam N-vinyl-2-valerolactam, 4-methyl-N-vinyl-2-pyrrolidone, 3,5-dimethyl-N-vinyl-2-caprolactam, N-vinyl-hexahydro-2-azepinone, N-vinyl-octahydro-2-azocinone, N-vinyl octahydro-2-azoninone and N-vinyl decahydro-2-azecinone, etc. Preference is given to using N-vinyl-2-pyrrolidone and/or N-vinyl-2-caprolactam.

The comonomer (B) for preparing cationic/pseudo-cationic non-homopolymer may be selected from a group of compounds having α,β-ethylenically unsaturated double bond and at least one cationogenic and/or cationic group per molecule. The compounds may be selected from the esters of α,β-ethylenically unsaturated mono and dicarboxylic acids with amino alcohols and in some cases the amino alcohols may be $C_2$-$C_{20}$-amino alcohols which are $C_1$-$C_8$ mono or dialkylated on the nitrogen atom of the amine functional group. The suitable acid components of these esters are, for example, acrylic acid, methacrylic acid, fumaric acid, maleic acid, itaconic acid, crotonic acid, maleic anhydride, monobutyl maleate alone or in combination thereof. Acrylic acid, methacrylic acid and mixtures thereof are particularly useful.

Comonomers useful for preparing the rheology modifying crosslinked polymer (B) include N-tert-butylaminoethyl (meth)acrylate, N,N-dimethylaminomethyl(meth)acrylate, N,N-dimethylaminoethyl(meth)acrylate, N,N-diethylaminoethyl(meth)acrylate, N,N-dimethylaminopropyl(meth)acrylate, N,N-diethylaminopropyl(meth)acrylate and N,N-dimethylaminocyclohexyl(meth)acrylate, dimethylaminomethyl acrylate, diethylaminomethyl acrylate, dimethylaminoethyl acrylate, dimethylaminobutyl acrylate, dimethylaminobutyl methacrylate, dimethylaminoamyl methacrylate, diethylaminoamyl methacrylate, dimethylaminohexyl acrylate, diethylaminohexyl methacrylate, dimethylaminooctyl acrylate, dimethylaminooctyl methacrylate, diethylaminooctyl acrylate, diethylaminooctyl methacrylate, dimethylaminodecyl methacrylate, dimethylaminododecyl methacrylate, diethylaminolauryl acrylate. diethylaminolauryl methacrylate, dimethylaminostearyl acrylate, dimethylaminostearyl methacrylate, diethylaminostearyl acrylate and diethylaminostearyl methacrylate. Particularly useful are N-tert-butylaminoethyl (meth)acrylate and N,N-dimethylaminoethyl(meth)acrylate. Particular preference is furthermore given to N,N-dimethylaminoethyl acrylate and N,N-dimethylaminoethyl methacrylate.

Further, the suitable amide based comonomers (B) for preparing cationic/pseudo-cationic non-homopolymer may be selected from a group of compounds including, but not limited to, α,β-ethylenically unsaturated mono and dicarboxylic acids with diamines having at least one primary or secondary amino group in it. The choice is provided to diamines which have one tertiary and one primary or secondary amino group. The most appropriate monomers would include, but are not limited to, N-tert-butylaminoethyl (meth)acrylamide, N-[2-(dimethylamino)ethyl]acrylamide, N-[2-(dimethylamino)ethyl]methacrylamide, N-[3-(dimethylamino)propyl]acrylamide, N-[3-(dimethylamino)propyl]methacrylamide, N-[4-(dimethylamino)butyl]acrylamide, N-[4-(dimethylamino)butyl]methacrylamide, N-[2-(diethylamino)ethyl]acrylamide, N-[4-(dimethylamino)cyclohexyl]acrylamide and N-[4-(dimethylamino)cyclohexyl]methacrylamide, N-[12-(dimethylamino)dodecyl]methacrylamide, N-[18-(dimethylamino)octadecyl]methacrylamide, N-[8-(dimethylamino)octyl]methacrylamide, N-[7-(dimethylamino)heptyl]acrylamide, N-[14-(dimethylamino)tetradecyl]acrylamide, N-[3-(dimethylamino)propyl] methacrylamide, N-[3-(diethylamino)propyl]acrylamide, N-[4-(dipropylamino)butyl]methacrylamide, N-[3-(methyl butyl amino)propyl]acrylamide, N-(2-[3-(dimethylamino) propyl]ethyl)acrylamide, N-(4-[4-(diethylamino)butyl]butyl)acrylamide. Special significance is given to N-[3-(dimethylamino)propyl]acrylamide, N-[3-(dimethylamino) propyl]methacrylamide (DMAPMA) and mixtures thereof.

In a specific embodiment of the present invention, the comonomer for preparing cationic/pseudo-cationic non-homopolymer may be selected from a group of quaternized ammonium compounds such as diethyldiallyl ammonium chloride (DEDAAC) dimethyldiallyl ammonium chloride (DMDAAC), methacryloyloxy ethyl trimethyl ammonium methylsulfate (METAMS), methacrylamido propyl trimethyl ammonium chloride (MAPTAC), acryloyloxyethyl trimethyl ammonium chloride (AETAC), methacryloyloxyethyl trimethyl ammonium chloride (METAC), acrylamidometlylpropyl trimethyl ammonium chloride (AMPTAC), acrylamide methyl butyl trimethyl ammonium chloride (AMBTAC) and mixtures thereof. Particularly useful cationic-containing monomers are MAPTAC, DMDAAC, DEDAAC and METAC alone or copolymerized with acrylamide, methacrylamide and N,N-dimethylacrylamide.

According to another embodiment of the present invention, one or more various cationic polymers belonging to "polyquaternium" (PQ) family of polymers may be employed to prepare the sprayable composition of high molecular weight charged polymers and wherein the selected high molecular weight cationic polyquaternium compounds is paired with one or more rheology modifying anionic polymer. The suitable PQ compounds include, but are not limited to; PQ-2, PQ-4, PQ-5, PQ-6, PQ-7, PQ-8, PQ-9, PQ-10, PQ-11, PQ-14, PQ-16, PQ-17, PQ-18, PQ-19, PQ-20, PQ-21, PQ-22, PQ-24, PQ-27, PQ-28, PQ-29, PQ-31, PQ-32, PQ-37, PQ-39, PQ 41, PQ-42, PQ-44, PQ-46, PQ-47, PQ-48, PQ-49, PQ-50, PQ-55, PQ-69 and other quaternary ammonium compounds are listed in the *CTFA Cosmetic Ingredient Handbook, First Edition,* on pages 41-42, incorporated herein by reference, and are described in the "History of Polymers in Haircare," Cosmetics and Toiletries, 103 (1988), incorporated herein by reference. Other synthetic polymers that may be used with the present invention can be referenced in the *CTFA Dictionary, Fifth Edition,* 2000, incorporated herein by reference.

The commercially available high molecular weight polymers of the present include, but are not limited to: poly(N-vinyl-2-pyrrolidone-co-dimethyl aminopropyl methacrylamide)acrylates copolymer (Styleze® CC-10), poly(N-vinyl-2-pyrrolidone-co-dimethylaminoethyl methacrylate) copolymer (Copolymer 937), PQ-11 (Gafquat® 755N), PQ-55 (Styleze® W20), PQ-28 (Conditioneze® NT-20), all of which are sold into commercial trade by International Specialty Products (Wayne, N.J.).

In another embodiment of the present invention, the rheology modifying crosslinked anionic polymer is selected for complexing with an oppositely charged cationic comonomer. The crosslinked anionic polymer may be obtained by polymerization of the monomeric system comprising (i) a monomer selected from N-vinyl lactams, N-vinyl-2-pyrrolidones, N-vinyl imidazoles, N-vinyl formamide, N-vinyl acetamide or vinyl methylacetamide; and (ii) a ethylenically unsaturated mono- or dicarboxylic acid based comonomer selected from the group consisting of acrylic acid, methacrylic acid, ethacrylic acid, α-chloroacrylic acid, crotonic acid, maleic acid, itaconic acid, citraconic acid, mesaconic acid, glutaconic acid, aconitic acid and fumaric acid.

Other rheology modifying crosslinked anionic polymers useful herein include copolymers of alkyl vinyl ethers and maleic anhydride, preferably crosslinked polymers or this type. In these copolymers the vinyl ethers are represented by the formula R—O—CH=$CH_2$ wherein R is a $C_1$-$C_6$ alkyl group, preferably R is methyl. Preferred crosslinking agents are $C_1$-$C_{20}$ dienes, preferably $C_6$ to C16 dienes, and most preferably $C_8$ to $C_{12}$ dienes. A particularly preferred copolymer is poly(methyl vinyl ether-co-maleic anhydride) 1,10-butadiene crosslinked polymer. This polymer has the CTFA designation PVM/MA decadiene cross-polymer and is commercially available as Stabileze™ 06 from International Specialty Products (Wayne, N.J.). Additionally, the crosslinked homopolymers may be selected from the group consisting of acrylic acid, methacrylic acid, ethacrylic acid, and mixtures thereof, with acrylic acid being most preferred. The examples for commercially available homopolymers useful herein include the carbomers, which are homopolymers of acrylic acid crosslinked with allyl ethers of sucrose or pentaerytritol. The carbomers are available as the Carbopol® 900 series from B.F. Goodrich. Anionic acrylate polymers, e.g., polymers sold under the trade name Aculyn series may also be employed herein as rheology modifying agents.

Non-limiting examples of rheology modifying anionic polymers of the present invention include Carbomer® 940 (Carbomer), UltraThix™ P-100 (acrylic acid/VP Crosspolymer), Stabileze® QM (PVM/MA decadiene crosspolymer), RapiThix®A-60 (sodium polyacrylate (and) hydrogenated polydecene (and) Trideceth-6) and/or Aculyn 28 (acrylates/beheneth-25 methacrylate copolymer).

The following complexes are non-limiting examples of complexes that are useful in accordance with the present application:
(i) (A) Vinylpyrrolidone/dimethylaminopropyl methacrylamide copolymer; and
   (B) Vinylpyrrolidone/acrylic acid crosslinked copolymer.
(ii) (A) Cationic polyquaternium-55; and
   (B) Vinylpyrrolidone/acrylic acid crosslinked copolymer.
(iii) (A) Vinylpyrrolidone/dimethylaminopropyl methacrylamide copolymer; and
   (B) Decadiene crosslinked poly (methyl vinyl ether-co-maleic anhydride).
(iv) (A) Cationic polyquaternium-28; and
   (B) Decadiene crosslinked poly (methyl vinyl ether-co-maleic anhydride).
(v) (A) Vinylpyrrolidone/dimethylaminopropyl methacrylamide copolymer; and
   (B) crosslinked polyacrylates.
(vi) (A) Vinylpyrrolidone/dimethylaminoethyl methacrylate copolymer; and
   (B) Vinylpyrrolidone/acrylic acid crosslinked copolymer.
(vii) (A) Vinylpyrrolidone/acrylic acid crosslinked copolymer; and
   (B) Vinylpyrrolidone/dimethyl aminoethyl methacrylate copolymer
(viii) (A) Acrylates/beheneth-25-methacrylate copolymer; and
   (B) Vinylpyrrolidone/dimethylaminopropyl methacrylamide copolymer
(ix) (A) Sodium Polyacrylate hydrogenated polydecene trideceth-6; and (B) Vinylpyrrolidone/dimethylaminopropyl methacrylamide copolymer.

In accordance with certain embodiments of the present invention, the range for the weight % active of (A) high molecular weight charged polymers and (B) oppositely charged rheology modifying crosslinked polymer employed to prepare the complex comprising aqueous sprayable composition is about 0.10 to about 1.25 wt. %; more particularly about 0.20 to about 1.0 wt. %; most preferred range is about 0.25 to about 0.85 wt. %. Further the specific range of high molecular weight charged polymer may be about 0.50 to about 5.00 wt. %; preferred range is about 0.75 to about 4.00 wt. %; most preferred range is about 0.85 to about 3.00 wt. %.

The preferred droplet size distributions for spray applications are those wherein the dv(50) value is no more than about 175 μm, wherein dv(50) is the median droplet size of the distribution. More preferably, the dv(50) value is no more than about 150 μm, and most preferably, dv(50) is no more than about 125 μm. The droplet size distribution can, for example, be determined with the help of conventional or nonconventional atomizing equipment and a particle measurement unit based on laser beam diffraction, e.g., a Malvern particle sizer measuring device. Compositions that form a snow-like consistency, flakes, or foam (spray foam) upon exiting the capillary spray system are also preferred.

In another embodiment of the present invention, the particle size analysis of polyelectrolyte complex (PEC) having a microgel structure formed between a cationic polyquaternium polymer and an anionic polymer resulted in significantly higher particle sizes than the particle sizes of a complex prepared in accordance with some aspects of the present invention, wherein the complex is made between (A) high molecular weight charged polymers having a molecular weight of at least about 125,000 amu or more; and (B) an oppositely charged rheology modifying crosslinked polymer containing at least one carboxylic functional group.

The composition typically contains cosmetically acceptable solvents, preferably an aqueous, alcoholic, or aqueous alcoholic medium. Particularly useful are the lower alcohols with $C_1$ to $C_4$ atoms, such as ethanol and isopropanol, particularly those used for cosmeceutical purposes. Additional co-solvents, organic solvents or a mixture of solvents with a boiling point of less than 400° C. can be present from about 0.1% to 95% (w/w), and more preferably from about 1% to 55% (w/w). Unbranched or branched hydrocarbons such as n-pentane, hexane, isopentane, and cyclic hydrocarbons such as cyclopentane and cyclohexane are particularly suitable as additional co-solvents. These volatile hydrocarbons can also be used as propellants. Other, especially preferred water-soluble solvents include, without limit, polyols such as glycerol, ethylene glycol, and propylene glycol in a quantity of up to 95% (w/w).

Alternatively, the sprayable aerosol composition employs from about 0.01% to about 75% (w/w) of propellant selected from: aliphatic hydrocarbons, nitrous oxide, $CO_2$, difluoroethane, trichlorofluoromethane, dichlorodifluoromethane, dichlorotetrafluoroethane, monochlorodifluoromethane, trichlorotrifluoroethane, dimethyl ether, propane, n-butane, isobutane, 2,2-dimethylpropane, isopentane and chlorofluorocarbons either singly or admixed. Other insoluble, compressed gases such as air, nitrogen, helium, and fully fluorinated oxetanes and oxepanes also are useful to deliver the compositions from aerosol containers.

Another embodiment of the present invention discloses a method for the preparation of sprayable composition comprising the steps:

i. Determining the amount of neutralizing agent required to adjust the pH of a rheology modifying crosslinked polymer, at the level to be used in the finished formulation in solution to within the range 5.5 to 8.5;
ii. Determining the amount of solvent to be used in the final, sprayable composition;
iii. Mixing and dissolving said rheology modifier of about 45% to about 75% of said solvent in one vessel;
iv. Adding about half of said neutralizing agent to the first vessel and mixing;
v. Mixing and dissolving said high molecular weight charged polymer of about 25% to about 55% of said solvent in a second vessel, the amount of which is specified in step (ii);
vi. Adding about half of said neutralizing agent to the second vessel and mixing;
vii. Adding the solution from step (v) to the solution from step (iii) while avoiding aeration, and mixing until uniform; and
viii. Optionally, adding any additional formulation ingredients and mixing until uniform.

The solvent in this process may be water, alcohols, branched hydrocarbons, unbranched hydrocarbons, and blends thereof.

The sprayable composition of the present invention may further comprise one or more optional constituents chosen from surfactants, perfumes, preservatives, UV protectants, chelating agents, cleansing agents, wetting agents, conditioning ingredients, flexibility enhancers, split modifiers, conditioning ingredients, humectants, propellants, compressed gases, proteins, amino acids, shine enhancers, neutralizing agents, texturizing agents, water-proofing agents, solubilizers, suspension agents, suspended materials, cosmetically acceptable ingredients such as emulsifiers, surfactants, preservatives, perfume oils, thickeners, hair polymers, hair and skin conditioners, graft polymers, water-soluble or dispersible silicone-containing polymers, light protection agents, bleaches, gel formers, care agents, colorants, tinting agents, tanning agents, dyes, pigments, bodying agents, moisturizers, refatting agents, collagen, protein hydrolyzates, lipids, antioxidants, defoamers, antistats, softeners, plasticizers; emollients, lubricants and penetrants; fragrances and perfumes; UV absorbers; anticorrosion agents; detackifying agents; combing aids and conditioning agents; antistatic agents; neutralizers; glossifiers; gelling agents; opacifiers; stabilizers; sequestering agents; chelating agents; pearling agents; and clarifying agents. These additives are commonly used in hair cosmetic compositions known heretofore. Selected additives are present in small, effective amounts to accomplish their function, and generally will comprise from about 0.1 to 10% by weight each and from about 0.1% to 20% by weight total, based on the weight of the composition.

The disclosed composition of the present invention is particularly useful for hair treatment. Within this context the term "hair spray" refers to compositions sprayed onto the hair. These compositions can be used for hair care purposes such as working spray, finishing spray, blow-dry protectant spray, flat-iron spray, thermal protectant spray, split-end mending spray, conditioning spray, and curl-enhancing spray. Additionally, these products can be hair-rinse products such as leave-on or rinse-off products; agents for the temporary reshaping and/or stabilizing of the hairstyle, for example hair lacquers, hair gels, hair waxes, styling creams, etc.; permanent, semi-permanent, or temporary hair colorants, for example oxidative hair colorants or nonoxidative hair tinting agents or hair bleaching agents; permanent hair restructuring agents, for example in the form of a mildly alkaline or acidic permanent wave or hair straightening agents containing a reducing agent, or in the form of permanent wave fixing agents containing an oxidizing agent.

The compositions of the present invention may be used in conventional methods to provide the required hair-care benefits. Those methods usually involve application of an effective amount of the product to wet, slightly damp or dry hair before or after optional styling methods, such as blow-drying, rollers, curling, flat-ironing, brushing, combing, teasing, setting, braiding, or waving. The application of the product is normally effected by spraying or atomizing the product using an appropriate device, e.g. a mechanical pump spray, a pressurized aerosol container, or other appropriate means. Other hair styling or hair-care compositions including tonics, foam, cream, emulsion, suspension, lotions, milk and gels, are typically dispensed from a conventional bottle or tube, and applied directly to the hair or first dispensed to the hand and then applied to the hair. The composition is then dried or allowed to dry. By "effective amount" is meant an amount sufficient to provide the hair hold and style benefits desired. In general, from about 0.5 g to about 30 g of product is applied to the hair, depending upon the particular product formulation, dispenser type, length of hair, and type of hair style.

Alternatively, the sprayable composition of the present invention can be used in various other fields including but are not limited to personal care, skin care, oral care, sun care, nail care, coatings, inks, household and industrial, biocides, pesticides, insecticides, antimicrobial agents, cleaning, disinfectant, pharmaceutical and/or paints.

In another aspect, the invention provides a method for creating a spray, wherein the above described complex is actuated to create droplets. Methods for actuating the complex composition are known to one skilled in the art, and include: a pump sprayer, a bag on valve system, a bag in can system, a sleeve in can system, as well as the traditional aerosol system.

Further, the present invention is illustrated in detail by way of the below given examples. The examples are given herein for illustration of the invention and are not intended to be limiting thereof.

EXAMPLES

Example 1

Various Complexes of a High Molecular Weight Charged Polymer and an Oppositely Charged, Rheology Modifying Crosslinked Polymer

| high molecular weight charged polymer | active addition level (w/w) | rheology modifying crosslinked polymer | active addition level (w/w) |
|---|---|---|---|
| poly(N-vinyl-2-pyrrolidone-co-dimethylaminopropyl methacrylamide) (Styleze ® CC-10) | 1.00% | poly(acrylic acid) crosslinked polymer (Carbomer ® 940) | 0.35% |
| poly(N-vinyl-2-pyrrolidone-co-dimethylaminopropyl methacrylamide) (Styleze ® CC-10) | 1.00% | poly(acrylic acid-co-N-vinyl-2-pyrrolidone) crosslinked polymer (UltraThix ™ P-100) | 0.75% |
| poly(N-vinyl-2-pyrrolidone-co-dimethylaminopropyl methacrylamide) (Styleze ® CC-10) | 1.00% | poly(methyl vinyl ether-co-maleic anhydride) 1,10-butadiene crosslinked polymer (Stabileze ® QM) | 0.50% |
| poly(N-vinyl-2-pyrrolidone-co-dimethylaminopropyl methacrylamide) (Styleze ® CC-10) | 1.00% | sodium polyacrylate (and) hydrogenated polydecene (and) trideceth-6 crosslinked polymer (RapiThix ® A-60) | 0.30% |
| poly(N-vinyl-pyrrolidone-co-dimethylaminopropyl methacrylamide) (Styleze ® CC-10) | 1.00% | poly(acrylates-co-beheneth-25 methacrylate) crosslinked polymer (Aculyn ® 28) | 0.50% |
| polyquaternium-55 (Styleze ® W) | 1.00% | poly(acrylic acid-co-N-vinyl-2-pyrrolidone) crosslinked polymer (UltraThix ™ P-100) | 0.75% |
| poly(N-vinyl-2-pyrrolidone-co-dimethylaminoethyl methacrylate) copolymer 937 | 1.00% | poly(acrylic acid-co-N-vinyl-2-pyrrolidone) crosslinked polymer (UltraThix ™ P-100) | 0.75% |
| polyquaternium-28 (Conditioneze ® NT-20) | 1.00% | poly(methyl vinyl ether-co-maleic anhydride) 1,10-butadiene crosslinked polymer (Stabileze ® QM) | 0.50% |
| polyquaternium-11 (Gafquat ® 755N) | 1.00% | poly(acrylic acid) crosslinked polymer (Carbomer ® 940) | 0.30% |

Example 2

Compositions Comprising a Complex of a Rheology Modifying Crosslinked Polymer and High Molecular Weight Charged Polymer

| ingredient | addition level (% w/w) | | | | |
|---|---|---|---|---|---|
| | 1 | 2 | 3 | 4 | 5 |
| deionized water | 91.65 | 94.00 | 87.00 | 87.00 | 87.15 |
| Na$_2$EDTA | 0.10 | | 0.10 | 0.10 | 0.10 |
| UltraThix ™ P-100 | 0.75 | — | — | — | — |

-continued

| ingredient | addition level (% w/w) | | | | |
|---|---|---|---|---|---|
| | 1 | 2 | 3 | 4 | 5 |
| Stabileze ® QM | — | — | 0.50 | — | — |
| Carbopol ® 940 | — | — | — | 0.50 | 0.35 |
| NaOH (10%) | 1.50 | — | 1.40 | 1.40 | 1.40 |
| Styleze ® CC10 | — | — | 10.00 | 10.00 | 10.00 |
| Styleze ® W 20 | 5.00 | 5.00 | — | — | — |
| Optiphen ® | 1.00 | 1.00 | 1.00 | 1.00 | 1.00 |
| Total | 100.00 | 100.00 | 100.00 | 100.00 | 100.00 |
| Sprayability | diffuse | stream | diffuse | stream | diffuse |

FIG. 1 is a graph of particle size distribution for the compositions of Example 2, measured with the following parameter: pump precision: P1D, 0.18 mL, Santos Actuator, 0.12" MBU Neural Insert, Jumbo dip tube, particle size distribution measured by Malvern SprayTec RTS 5214.

Example 3

Compositions Comprising a Complex of a Rheology Modifying Crosslinked Polymer and a High Molecular Weight Charged Polymer

| ingredient | A | B | C |
|---|---|---|---|
| | addition level (% w/w) | | |
| deionized water | 86.65 | 96.65 | 89.00 |
| Na₂EDTA | 0.10 | 0.10 | — |
| UltraThix ™ P-100 | 0.75 | 0.75 | — |
| NaOH (10%) | 1.50 | 1.50 | — |
| Styleze ® CC10 | 10.00 | — | 10.00 |
| Optiphen ® | 1.00 | 1.00 | 1.00 |
| Total | 100.00 | 100.00 | 100.00 |

Figure 2:
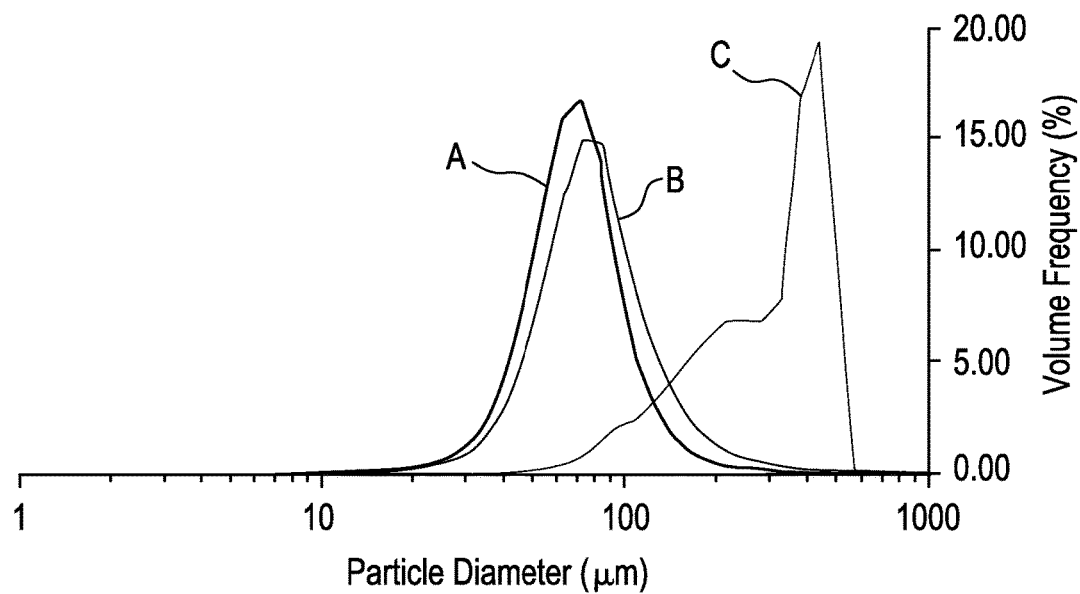
FIG. 2 is a graphical illustration of particle size distribution of compositions of Example 3.

FIG. 2 is a graph of particle size distribution for the compositions of Example 3, measured with the following parameter: pump precision: P1D, 0.18 mL, Santos Actuator, 0.12" MBU Neural Insert, Jumbo dip tube, particle size distribution measured by Malvern SprayTec RTS 5214.

Example 4

Compositions Comprising Complex of Rheology Modifying Agent and High Molecular Weight Charged Polymer

| ingredient | addition level (% w/w) | | |
|---|---|---|---|
| | A | B | C |
| deionized water | 92.00 | 92.00 | 92.15 |
| Na₂EDTA | 0.10 | 0.10 | 0.10 |
| Stabileze ® QM | 0.50 | 0.50 | — |
| Carbopol ® 940 | — | — | 0.35 |
| NaOH (10%) | 1.40 | 1.40 | 1.40 |
| Styleze ® W 20 | — | 5.00 | 5.00 |
| Conditioneze ® NT20 | 5.00 | — | — |
| Optiphen ® | 1.00 | 1.00 | 1.00 |
| Total | 100.00 | 100.00 | 100.00 |

Example 5

Sprayability and On-Hair Performance of Four Compositions

Carbomer®-940 (control 1),
Styleze® CC-10 at 0.10% addition level (control 2),
Styleze® CC-10 at 1.0% addition level (control 3) and
a complex of 0.35% Carbomer®-940:1.0% Styleze® CC-10 (a composition of the invention)

Figure 3:
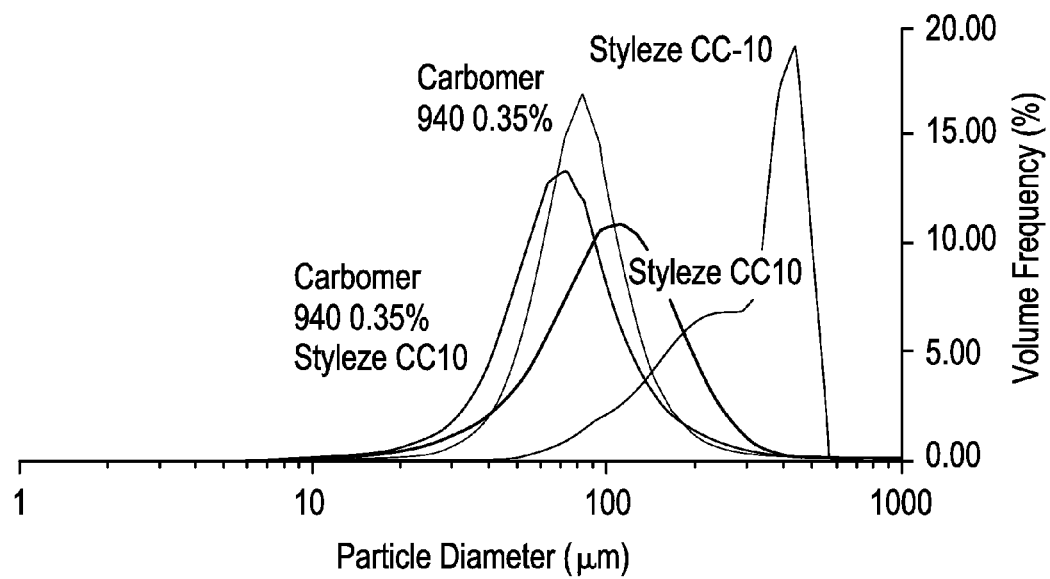
FIG. 3 is a graphical illustration of particle size distribution of compositions of Example 5.

FIG. 3 is a graph of particle size distribution for the compositions of Example 5, measured with the following parameter: pump precision: P1D, 0.18 mL, Santos Actuator, 0.12" MBU Neural Insert, Jumbo dip tube, particle size distribution measured by Malvern SprayTec RTS 5214.

Figure 4:
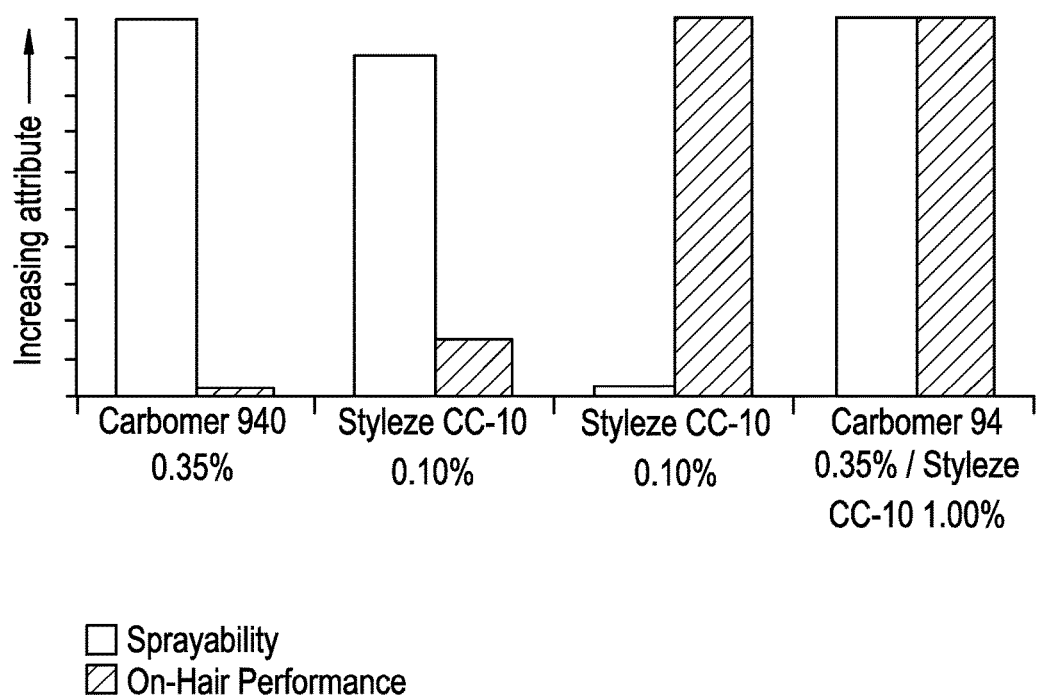
FIG. 4 is a graphical illustration (Bar Graph) of sprayability and on-hair performance for compositions of Example 5.

FIG. 4 is a bar graph of sprayability and on-hair performance for the compositions of Example 5.

Example 6

Figure 5:
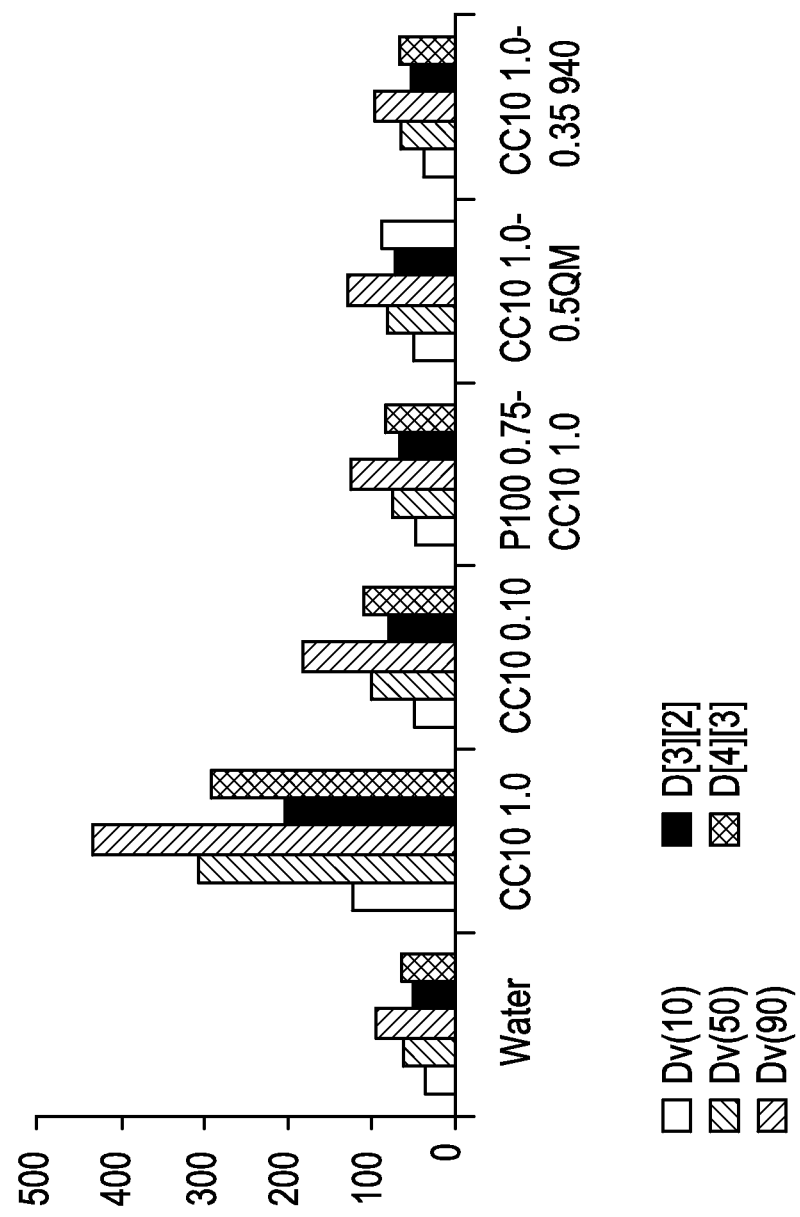
FIG. 5 is a graphical illustration of Complexes of Styleze CC-10 (1.0%) with various rheology modifying anionic microgels vs. water (control).

Complexes of Styleze® CC-10 (1.0%) with various rheology modifying anionic microgels allow for particle size distributions similar to a water control (FIG. 5). The non-complexed polymer can achieve a comparable distribution at a fraction of the complexed polymer (0.10% solids).

Example 7

Figure 6:
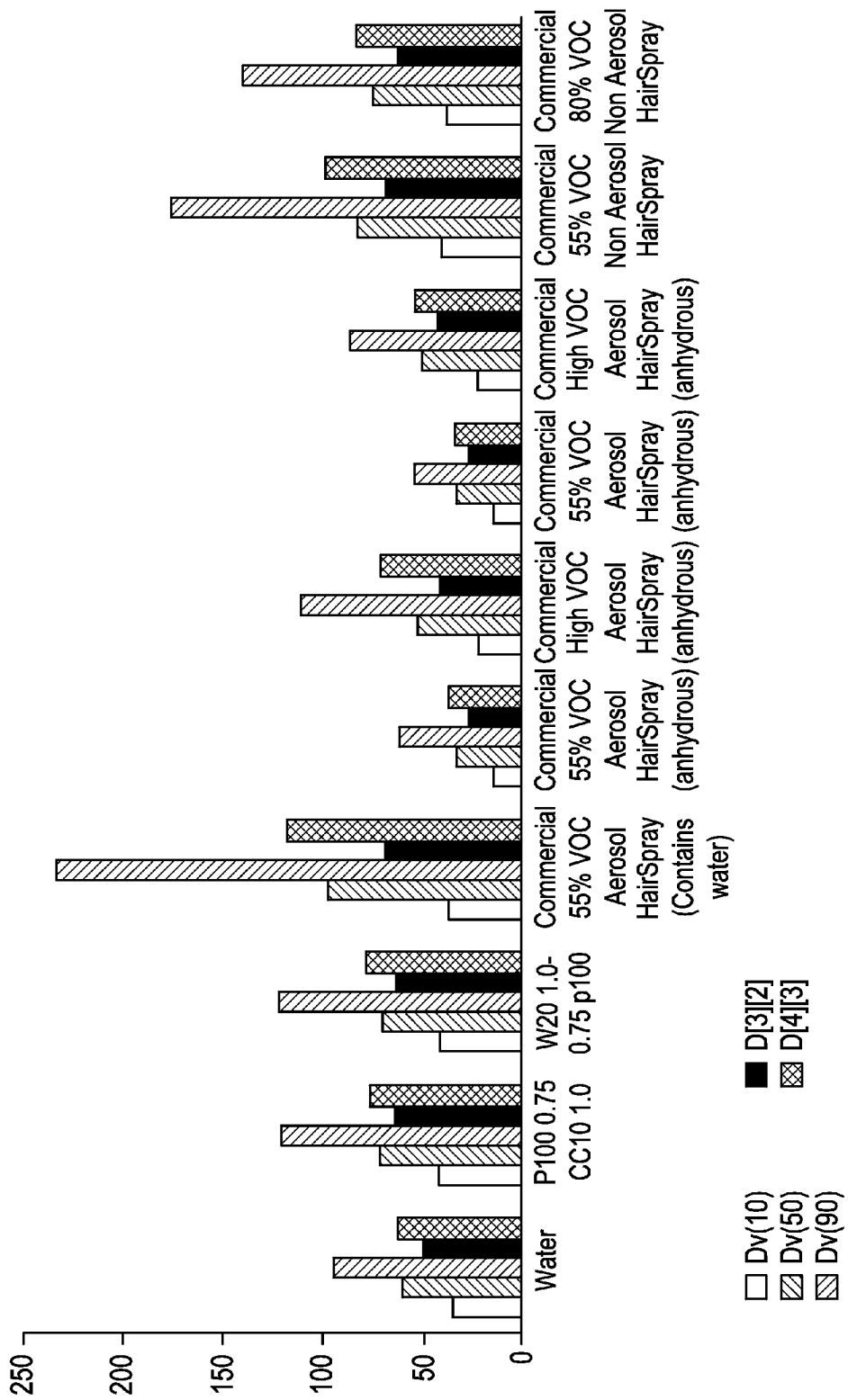
FIG. 6 is a graphical illustration of Complexes of Styleze CC-10 (1.0%) and Styleze W20 (1.0%) with various rheology modifying anionic microgels vs. water control and commercially available hair sprays.

Complexes of Styleze® CC-10 (1.0%) and Styleze® W20 (1.0%) with a Rheology Modifying Anionic Microgel Allow for a Distribution Similar to a Water Control and Commercially Available Hair Sprays (FIG. 6).

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope and spirit of this invention.

What is claimed is:

1. A sprayable composition comprising: a complex of
(A) at least one anionic, pseudo-anionic, cationic or pseudo-cationic polymer having a molecular weight of 250,000 amu or more; and (B) at least one cationic, pseudo-cationic, anionic or pseudo-anionic rheology modifying crosslinked polymer having at least one carboxylic functional group, wherein, said complex is selected from the group consisting of:
  (i) poly(N-vinyl-2-pyrrolidone-co-dimethylaminopropylmethacrylamide) copolymer and poly(N-vinyl-2-pyrrolidone-co-acrylic acid) crosslinked copolymer;
  (ii) PQ-55 and poly(N-vinyl-2-pyrrolidone-co-acrylic acid) crosslinked copolymer;
  (iii) poly(N-vinyl-2-pyrrolidone-co-dimethylaminopropylmethacrylamide) copolymer and poly(maleic anhydride-co-methylvinylether) 1,10-butadiene crosslinked copolymer;
  (iv) poly(N-vinyl-2-pyrrolidone-co-dimethylaminopropylmethacrylamide) copolymer and crosslinked polyacrylates; and
  (v) poly(N-vinyl-2-pyrrolidone-co-dimethylaminoethyl methacrylate) copolymer and poly(N-vinyl-2-pyrrolidone-co-acrylic acid) crosslinked copolymer,
wherein, said sprayable composition provides a spray with a median droplet size, dv(50), of less than about 175 μm.

2. The composition of claim 1 wherein said (A) is present from about 0.5% to about 5.0% (w/w), and wherein said (B) is present from about 0.1% to about 1.25% (w/w).

3. The composition of claim 1, further comprising at least one additive selected from the group consisting of: surfactants, perfumes, preservatives, UV protectants, chelating agents, cleansing agents, wetting agents, conditioning ingredients, flexibility enhancers, split modifiers, conditioning ingredients, humectants, propellants, compressed gases, proteins, amino acids, shine enhancers, neutralizing agents, texturizing agents, water-proofing agents, solubilizers, suspension agents, suspended materials, cosmetically active ingredients, emulsifiers, surfactants, preservatives, perfume oils, thickeners, hair polymers, hair and skin conditioners, graft polymers, water-soluble silicone-containing polymers, light protection agents, bleaches, gel formers, care agents, colorants, tinting agents, tanning agents, dyes, pigments, bodying agents, moisturizers, refatting agents, collagen, protein hydrolyzates, lipids, antioxidants, defoamers, antistats, emollients, softeners, and blends thereof.

4. The composition of claim 1 is in the form of a gel, foam, cream, suspension, lotion, aerosol, pump spray, emulsion, or milk.

5. The composition of claim h wherein said composition is a personal care or performance chemicals composition.

6. The composition of claim 5, wherein said personal care composition is a hair spray, skin care, sun care, oral care, or nail care composition.

7. The composition of claim 6, wherein said personal care composition is a hair spray.

8. The composition of claim 5, wherein said performance chemicals composition is coatings, inks, paints, biocides, pesticides, insecticides, antimicrobial, cleaning, disinfectant, sanitary, or paint composition.

9. A method of enhancing the on-hair performance of a hair spray, said method comprising the steps:
(i) Providing the sprayable composition of claim 1;
(ii) Actuating said composition to produce a spray; and
(iii) Applying said spray to a user's hair.

* * * * *